United States Patent [19]

Haast

[11] Patent Number: 4,976,693
[45] Date of Patent: Dec. 11, 1990

[54] DEGRADABLE SYRINGE

[76] Inventor: William E. Haast, Miami Serpentarium Laboratories, Innovation Center, University of Utah Research Park, 419 Wakara Way, #100, Salt Lake City, Utah 84108

[21] Appl. No.: 450,528
[22] Filed: Dec. 14, 1989
[51] Int. Cl.⁵ .............................................. A61M 5/00
[52] U.S. Cl. .................................................... 604/110
[58] Field of Search ............... 604/110, 187, 240, 241, 604/242, 243, 88

[56] References Cited

U.S. PATENT DOCUMENTS 4,059,109 11/1977 Tischlinger ........................... 604/88
4,781,683 11/1988 Wozniak et al. ..................... 604/110
4,816,021  3/1989 Johnson ............................... 604/110

Primary Examiner—John D. Yasko
Attorney, Agent, or Firm—Kenneth E. Darnell

[57] ABSTRACT

A syringe which can be filled immediately before use or which can be pre-filled and which is rendered inoperative after a single use without requiring a deliberate action by the user, the invention has certain critical portions formed of a material which degrades at least partially upon contact with the medication or solution injected on a first use through the syringe, thereby rendering the syringe unusable after the first use. In a primary embodiment, portions of the present syringe which mount a needle to the main body of the syringe are formed of a material which is at least partially soluble in the medication or solution used with the syringe or which absorbs the medication or solution, thereby preventing the needle from being retained in an operative position on the syringe.

26 Claims, 3 Drawing Sheets

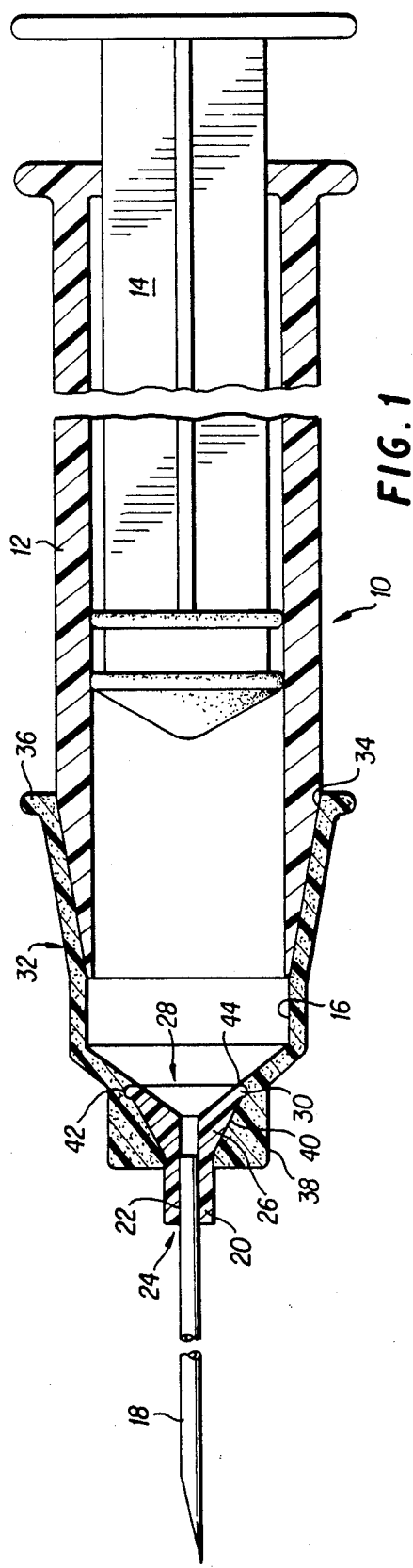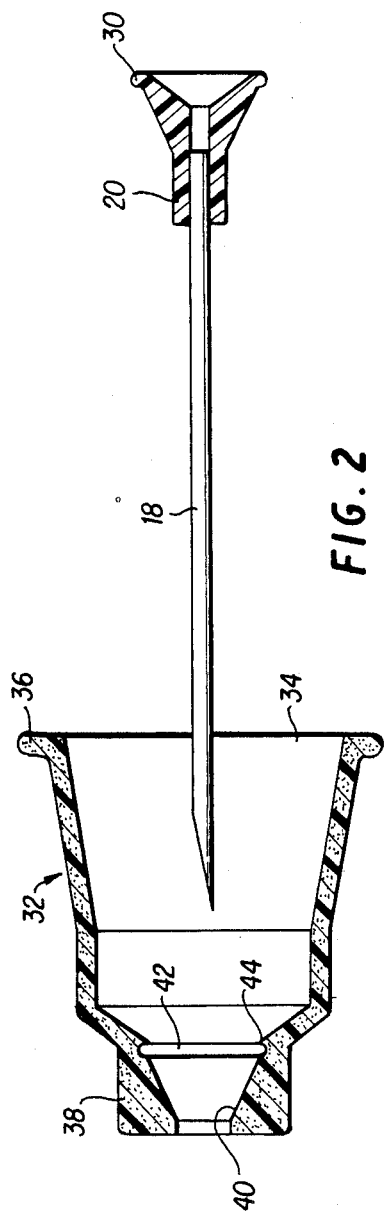

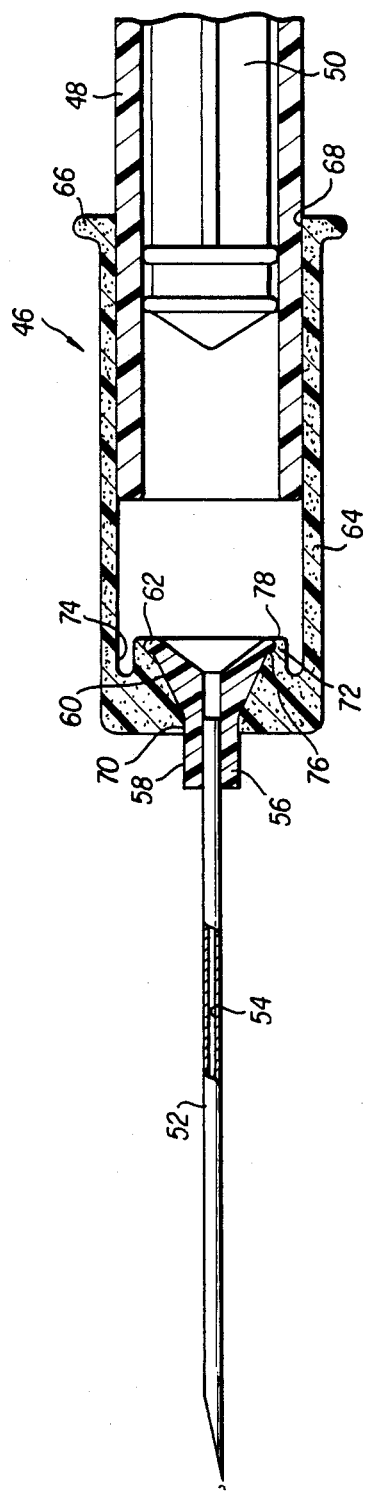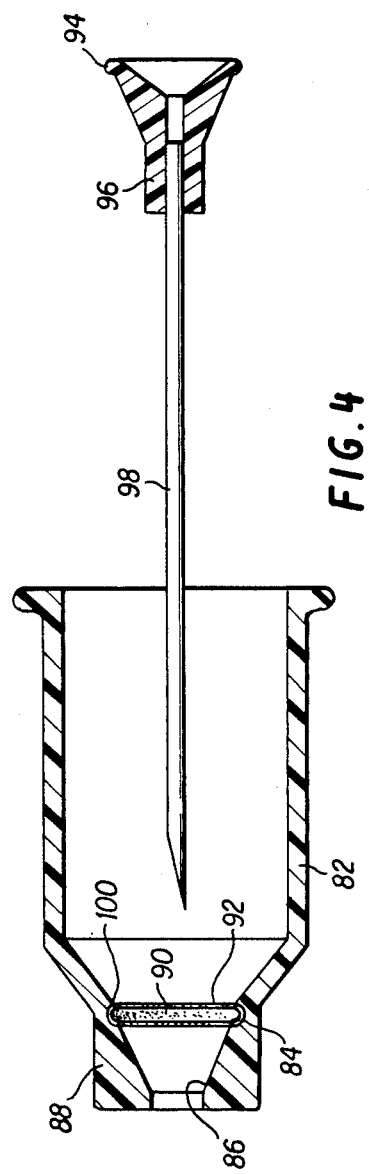

DEGRADABLE SYRINGE

BACKGROUND OF THE INVENTION

I. Field of the Invention

The invention relates generally to syringes and similar devices for injection of fluids into an organism or other entity and particularly relates to a degradable or self-destructing syringe capable of only a single use.

II. Description of the Prior Art

Transmission of diseases such as acquired immune deficiency syndrome (AIDS), hepatitis, etc. often occurs due to the sharing of syringes by intravenous drug users. In order to prevent the spread of various diseases by this transmission route, it has long been known in the art to provide syringes and similar devices which become inoperative after only a single use. Most such devices are mechanical in nature with the syringe needle or other portion of the syringe being destroyed either by virtue of the normal injection motion when the syringe is used or by some deliberate action by a user. Syringes which "destruct" without any deliberate action on the part of a user would, of course, be more effective in preventing disease transmission by intravenous drug users since such persons usually wish to maintain a syringe in useable condition so that the syringe may be shared. Again, certain syringes have previously been developed which become inoperative after a single use although most such devices are impractical due to complexity and expense. The art has, however, advanced to a state whereby certain syringes are known which become inoperative after only one or after only a few uses and which are not mechanically complex and which require little structural variation from the structure of a typical syringe. In U.S. Pat. No. 4,781,683 to Wozniak et al, a single-use, self-annuling injection syringe is disclosed which includes a hydrophilic expansion plug positioned in the outlet flow channel of the syringe. The expansion plug expands after being exposed to a material containing water and thereby renders the syringe inoperative by blocking the outlet flow channel of the syringe. As a further example, Johnson provides in U.S. Pat. No. 4,816,021, a self-destructing hypodermic device intended for only a single use. In Johnson, at least some portion of the syringe, such as the casing, plunger or the like is comprised of a material which is at least partially soluble in the medications or solutions intravenously injected through use of the device. Accordingly, those portions of the Johnson syringe destruct after only one or a few uses and therefore do not allow continued use of the syringe.

The need continues to exist in the art for a single-use syringe which readily and rapidly degrades and becomes inoperative after a single use without the requirement for any deliberate action on the part of a user of the syringe. The need further exists for a syringe which is not mechanically complex or expensive and which has a structure which varies as little as possible from the structure of a typical syringe. A need further exists in the art for a pre-filled syringe which will become unuseable after only a single use. The present invention addresses these needs in the art by providing a syringe having a structure which is similar to the structures of typical syringes and which is therefore readily fabricated but which also becomes inoperative after only a single use or only a few uses without requiring a deliberate action on the part of a user. In order to accomplish these objectives, the syringe of the present invention mounts a needle to a main body of a syringe by means of structural portions which are formed of a material which is at least partially soluble in or absorbant by the medication or solution used with the syringe, thereby preventing the needle from being retained in an operative position on the syringe after a first use of the syringe.

SUMMARY OF THE INVENTION

The invention provides in several embodiments syringes and similar devices which can be filled immediately before use or which can be pre-filled. Actual use of the syringes of the invention cause the syringes to become inoperative after either a single use or after only a few uses without the requirement for deliberate action on the part of the user. The concept underlying the several embodiments of the invention is the formation of structure mounting a syringe needle to a body of a syringe from a material which "self-destructs" after exposure to water and/or alcohol-based medications or the like. The materials so chosen are at least partially soluble in the medication or solution or absorb the medication or solution, thereby causing the needle-mounting structure to cease to mount the needle in an operative relation with the main body of the syringe. The syringe is thus caused to become inoperative. Preferred materials from which these critical needle-mounting portions of the syringe are formed include collodion materials which include collagens and similar materials. Of particular interest are materials which are at least partially soluble in the medications or solutions used with the syringe.

In order to produce a syringe structure which "degrades" or "self-destructs" after only a single use, it is necessary to utilize the collodion or other materials in areas which contact the medication or solution only as said medication or solution is injected. Further, the portions of the syringe structure formed of the collodion materials must be of a thickness such that even minimal contact with the solubilizing medication or solution will cause that structure mounting the needle to become inoperative to hold the needle in working relation with the remainder of the syringe. Accordingly, it is also necessary to maintain the solubilizing medication or solution out of contact with the soluble syringe structure so that premature destruction of the needle-mounting structure does not occur. In the case of a pre-filled syringe according to the invention, the medication or solution is maintained within the "barrel" of a syringe and only comes in contact with the soluble portions of the needle-mounting structure on injection of the medication or solution through the syringe.

Accordingly, it is an object of the invention to provide a syringe which can be filled immediately before use or which can be pre-filled and which is rendered inoperative after a single use without the requirement for a deliberate action by the user.

It is another object of the invention to provide a single-use syringe which is of minimum complexity and expense and which further requires little structural variation from the structure of a typical syringe.

Yet another object of the invention is to provide a practical single-use syringe formed of structure adaptable to use as a pre-filled syringe.

Further objects and advantages of the invention will become more readily apparent in light of the following detailed description of the preferred embodiments.

BRIEF DESCRIPTION OF THE DRAWINGS

FIG. 1 is an elevational view in section of a first embodiment of the invention illustrating only partially a syringe to which the device of the invention is mounted;

FIG. 2 is an assembly view in partial section of the several component portions of the present invention of FIG. 1;

FIG. 3 is an elevational view in partial section of a second embodiment of the invention illustrating structure for mounting a needle to a syringe (shown partially) according to the invention;

FIG. 4 is an elevational view in partial section of another embodiment of the invention illustrating particular mounting structure for a needle to a syringe; and, FIG. 5 is an elevational view in partial section of yet another embodiment of the invention illustrating a prefilled syringe and utilizing the needle-mounting structure of the invention.

DESCRIPTION OF THE PREFERRED EMBODIMENTS

Figure 5:
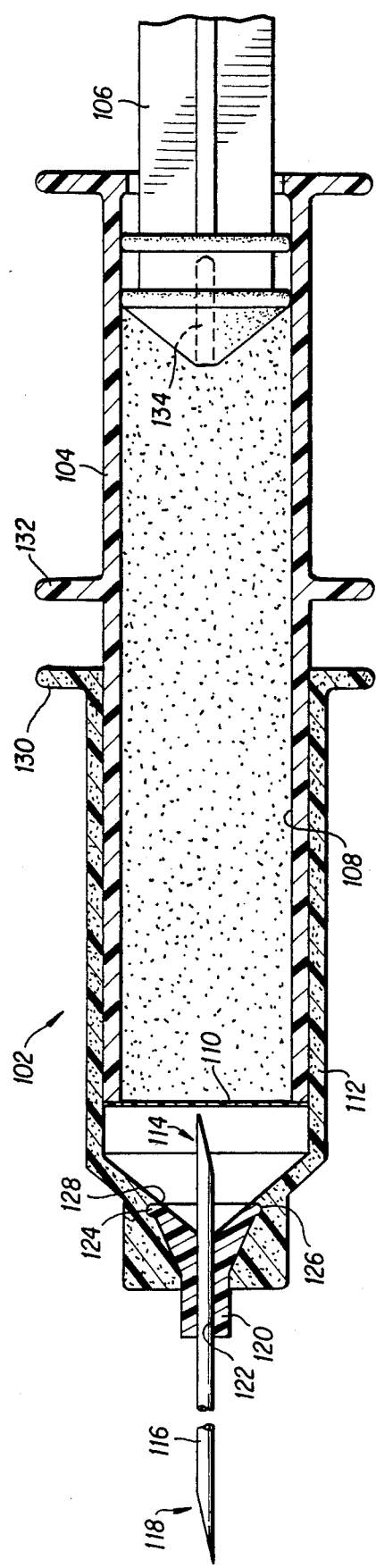

Referring now to the drawings and particularly to FIGS. 1 and 2, a hypodermic syringe is seen generally at 10 to be comprised of a barrel 12 and plunger 14, this structure being substantially conventional. The syringe 10 is of the type which is filled with a medication or solution immediately prior to use with the plunger 14 being moved to a position fully received within the barrel 12 (not shown) and moved outwardly to create a vacuum within chamber 16, thereby allowing a medication to be drawn through needle 18. The needle 18 is inserted into a solution or medication which is to be injected through use of the syringe 10. This filling of a conventional syringe is an exceedingly well-known process.

Conventionally, the needle 18 is formed of a hollow metal sheath and the barrel 12 and plunger 14 are conventionally formed of "plastic" or other material which is not reactive with the medication or solution with which the syringe 10 is filled.

The needle 18 can conveniently be mounted to a collar 20 which also can be formed of a "plastic" of substantially the same material which is used to form the barrel 12 or the plunger 14. The needle 18 is received within a central bore 22 formed within the collar 20. The collar 20 is substantially cylindrical in conformation at its distal end 24, the collar 20 enlarging in diameter to a frusto-conical portion 26 near the anterior end 28, the collar 20 terminating in an annular bead 30. The needle 18 does not have to be fully received within the bore 22 as is shown in FIG. 1.

The embodiment of the invention shown in FIGS. 1 and 2 has as its primary feature a mounting cuff 32 which receives one end of the barrel 12 at a first end and which receives the needle-mounting collar 20 at its other end. The mounting cuff 32 is substantially hollow and has an enlarged opening 34 formed in the end which receives one end portion of the barrel 12. The cuff 32 can be conical in conformation at the end receiving the barrel 12 in order to conform to and mount flushly onto the end of the barrel 12 which is received through the opening 34. The cuff can conveniently have an annular bead 36 which acts to facilitate handling of the syringe 10. The cuff 32 tapers from its conical portion to a substantially cylindrical portion which substantially defines the chamber 16. The cuff 32 further tapers to a shoulder 38 through which a bore 40 is formed, the bore 40 having a frusto-conical shape into which the frusto-conical portion 26 of the collar 20 fits. FIG. 2 provides an assembly view of the needle 18/collar 20 assembly prior to its being fitted into the bore 40.

At the inner end of the bore 40, the shoulder 38 has a groove 42 formed therein, the bead 30 of the collar 20 fitting into the groove 42 and essentially snap-fitting into said groove 42 in order to hold the needle 18/collar 20 assembly in place on the mounting cuff 32. The groove 42 is annular in conformation and essentially acts to hold the annular bead 30 of the collar 20 within said groove 42 by means of an annular friction nib 44.

In the embodiment of FIGS. 1 and 2, the entirety of the mounting cuff 32 is formed of a material which is at least partially soluble in the medication or solution which is to be injected through use of the syringe 10. This material can be a collodion material. The material can be one of a variety of collagens which is at least partially soluble in water and/or alcohol. The material can be gelatin or material similar to gelatin which begin dissolution within solvents such as water commonly used in medications and various solutions which may be injected through use of the syringe 10. Since the mounting cuff 32 is formed of this soluble material, the cuff 32 begins degrading as soon as the syringe 10 is filled with the medication or solution. However, the annular friction nib 44, since it comes to a relatively thin annular edge, degrades more rapidly than does the remainder of the cuff 32. Accordingly, after a single use of the syringe 10, the nib 44 has substantially degraded to the point that the collar 20 mounting the needle 18 no longer remains firmly in place within the mounting cuff 32 and cannot thereby maintain an operative position relative to the remaining portions of the syringe 10. In time, major portions of the cuff 32 will soften and thus degrade further. A first filling of a syringe 10 and a subsequent injection within a reasonable time can occur through use of the syringe 10. However, prolonged contact with an injectible solution softens the cuff 32 and especially the nib 44 within a sufficiently short period of time such that a second filling and use of the syringe 10 is prevented. The needle 18/collar 20 assembly disengages from the groove 42 and thus from a structurally adequate mounting relation with the cuff 32 such that the syringe 10 becomes inoperable when pressure is subsequently exerted on the needle 18 such as when a second injection is attempted.

As is shown in FIG. 3, a second embodiment of the invention is seen to comprise a syringe 46 conventionally formed of a barrel 48 and plunger 50 in a manner similar to the formation of the syringe 10 of FIGS. 1 and 2. A needle 52 conventionally formed of metal and having a lumen 54 through which the syringe 10 is both filled and evacuated is mounted by a collar 56 of a construction which is similar to that of the collar 20 of FIGS. 1 and 2. However, the collar 56 is formed of a substantially cylindrical body portion 58 which terminates anteriorly in a conical flange 60 having an annular bead 62 formed about the periphery of the flange 60. The collar 56 is preferably formed of a "plastic" material in a conventional manner as is the barrel 48 and the plunger 50.

The needle 52/collar 56 assembly is mounted to the syringe 46 by means of a mounting cuff 64. The cuff 64 is substantially cylindrical along its length and terminates at an end thereof receiving an end of the barrel 48 in an annular bead 66 which facilitates handling of the syringe 46. The end of the cuff 64 having the bead 66 has an opening 68 which allows receipt of an end of the barrel 48. The cuff 64 is substantially hollow except at that end of the cuff 64 opposite the end having the annular bead 66. At this other end, the cuff 64 is closed except for a central bore 70 through which the cylindrical portion of the collar 56 can be flushly received, the bore 70 expanding anteriorly to form a substantially conical portion which receives the conical flange 60 of the collar 56. At least part of the bore 70 and the conical portion of said bore 70 are formed within an internal shoulder portion 72 extending inwardly toward the hollow interior of the cuff 64, the shoulder portion 72 being surrounded with an annular trough-like groove 74 which is separated from a groove 76 formed at the terminating end of the conical portion of the bore 70. As is the case with the embodiment of FIGS. 1 and 2, the annular bead 62 of the collar 56 fits into the groove 76 and preferably in a snap-fitting fashion such that the needle 52/collar 56 assembly is positively mounted by the mounting cuff 64. A thin annular edge portion 78 of the shoulder portion 72 separates the bead 62 of the collar 56 from medication or solution which is drawn into the syringe 46 in a manner substantially identical to the drawing of medication or solution into the syringe 10 of FIGS. 1 and 2. Since the material from which the mounting cuff 64 is formed is the same as the materials from which the mounting cuff 32 of FIGS. 1 and 2, the medication or solution drawn into the syringe 46 and lying not only within the groove 74 but in general contact with the edge portion 78 toward the anterior of the cuff 64 causes the material from which the edge portion 72 is formed to readily begin at least partial dissolution when the syringe 46 is filled. Subsequent attempts to fill and use the syringe 46 are rendered ineffective by virtue of the at least partial dissolution of the edge portion 78 thereby preventing the needle 52/collar 56 assembly from being positively mounted to the syringe 46, thereby rendering the syringe inoperative.

Referring now to FIG. 4, a detailed view of a syringe generally shown at 80 is provided, the syringe 80 being substantially identical to the syringes 10 and 46 previously described. The syringe 80 further has a mounting cuff 82 which is similar in structure and function to the mounting cuff 32 of FIGS. 1 and 2. However, in the embodiment of FIG. 4, the mounting cuff 32 is formed of a "plastic" material which can be similar to or identical to the "plastic" material used to form syringe barrels, plungers, etc. In the mounting cuff 82 of FIG. 4, however, an annular raceway terminates bore 86 formed in shoulder 88 of the cuff 82. The raceway 84 is filled with a material such as that described above which is at least partially soluble in the medication or solution which is to be used in the syringe 80, this material being referred to at 90 and being shaped to provide an anterior continuation of the bore 86 and having a groove 92 formed in said material such that an annular bead 94 of collar 96 is received within the groove 92. The collar 96 is substantially identical to the collar 20 of FIGS. 1 and 2 and mounts a needle 98 in essentially the same fashion as the collar 20 mounts the needle 18 in FIGS. 1 and 2.

In the embodiment of FIG. 4, only the material 90 within the annular raceway 84 is formed of a soluble material, thereby allowing the mounting cuff 82 to be formed of a "plastic" material. Accordingly, the mounting cuff 82 can be formed integrally with a syringe barrel (not shown) if so desired for ease of manufacture.

The material 90 filling the annular raceway 84 can readily be shaped to have an annular friction nib 100 which functions essentially identically to the nib 44 described hereinabove relative to FIGS. 1 and 2.

Referring now to FIG. 5, a prefilled syringe is seen at 102 to comprise a barrel 104 and a plunger 106. In a known manner, the barrel 104 is prefilled with a medication or solution which is disposed within chamber 108 of the barrel 104. The barrel 104 has a frangible diaphragm 110 which seals its inner end in order to maintain the medication within the chamber 108. An anterior end of the barrel 104 is received within a mounting cuff 112, the mounting cuff 112 being formed of a material substantially identical to the material from which the mounting cuff 32 of FIGS. 1 and 2 and the mounting cuff 64 of FIG. 3 is formed, that is, the cuff 112 is formed of a material which is at least partially soluble within the medication or solution being held within the chamber 108. However, the mounting cuff 112 does not contact the medication or solution held within the chamber 108 until the diaphragm 110 is pierced by anterior end 114 of needle 116, the needle 116 having the usual distal end 118 used to pierce an individual or entity into which the medication or solution is injected. A collar 120 formed substantially identically to the collar 20 of FIGS. 1 and 2 mounts the needle 116 positively within a bore 122. The collar 120 terminates anteriorly in an annular bead 124 which is received within a groove 126 formed in the mounting cuff 112 in a manner which is substantially identical to the formation and function of the groove 42 formed in the cuff 32 of FIGS. 1 and 2. An annular friction nib 128 allows friction-fit of the collar 120 within the groove 126 of the cuff 112, the nib 128 being formed of a soluble material as aforesaid since the cuff 112 is so formed. However, it is to be understood that the prefilled syringe 102 could be formed with a mounting cuff 112 which is essentially identical in structure and operation to the mounting cuff 64 of FIG. 3 or the mounting cuff 82 of FIG. 4 without departing from the scope and spirit of the invention.

In operation, the barrel 104 is moved forwardly into the cuff 112 through use of beads 130 and 132 formed respectively on the cuff 112 and the barrel 104. This relative movement of the barrel 104 and the cuff 112 causes the anterior end 114 of the needle 116 to pierce the frangible diaphragm 110 and cause the medication or solution held within the chamber 108 to flow through the pierced diaphragm and into a position contacting inner surfaces of the mounting cuff 112 and particularly the annular nib 128 with the resulting initiation of softening of said portions of the cuff 112. The plunger 106 is then operated in a conventional manner to dispense the medication or solution through the needle 116. The plunger 106 can be formed with a bore shown in phantom at 134 such that the anterior end 114 of the needle 116 can be received into said bore 134 so that the plunger 106 may be fully extended.

Accordingly, the embodiment of FIG. 5 provides a prefilled syringe capable of a single use without the need for a deliberate act on the part of a user to render the syringe inoperative. In the syringe 102, a medication or solution is held within the barrel 104 of the syringe and out of contact with those portions of the syringe 102 which become at least partially soluble and soften on contact with the medication or solution. It is to be understood that other forms of a prefilled syringe can be readily devised in light of the disclosure herein provided without departing from the scope of the invention. Further, it can readily be seen that other embodiments of the inventive concept disclosed herein can be devised in light of the inventive concept so disclosed. Accordingly, the scope of the invention is to be determined by the definition provided by the appended claims.

What is claimed is:

1. In a syringe capable of injecting a medication or solution and having a needle, a barrel and a plunger, the improvement comprising:
   means for mounting the needle to the barrel, at least portions of the mounting means being formed of a material which is at least partially soluble in the medication or solution, contact between said portions of the mounting means and the medication or solution causing the mounting means to eventually become inoperable so that the syringe can be used only a single time, the mounting means comprising
   a collar mounting the needle and having an annular bead formed on one end of the collar; and,
   a mounting cuff at least portions of which are formed of a material which is at least partially soluble in the medication or solution, the cuff operatively connecting the barrel of the syringe with the collar which mounts the needle, the cuff having a groove formed therein for receiving the bead of the collar and positively holding the bead therein, contact between at least portions of the cuff surrounding and defining the groove with the medication or solution causing softening of said portions to prevent maintenance of the collar and thus the needle mounted by the collar in an operative position relative to the barrel of the syringe.

2. In the syringe of claim 1 wherein the collar is formed of a substantially rigid plastic material which is inert to the medication or solution.

3. In the syringe of claim 2 wherein the mounting cuff is formed of the material which is at least partially soluble in the medication or solution.

4. In the syringe of claim 3 wherein the material is selected from the group consisting of collagens and gelatin.

5. In the syringe of claim 2 wherein portions of the mounting cuff defining the groove are formed of the material which is at least partially soluble in the medication or solution.

6. In the syringe of claim 5 wherein the material is selected from the group consisting of collagens and gelatin.

7. In the syringe of claim 1 wherein that portion of the mounting cuff defining the groove comprises an interior shoulder portion of the cuff and has a second annular groove formed between the shoulder portion and inner walls of the cuff, the medication or solution contacting surfaces of the second annular groove to soften said portions.

8. In the syringe of claim 7 wherein the collar is formed of a substantially rigid plastic material which is inert to the medication or solution.

9. In the syringe of claim 8 wherein the material is selected from the group consisting of collagens and gelatin.

10. In the syringe of claim 1 wherein the mounting cuff is formed of a substantially rigid plastic material which is inert to the mediciation or solution, the cuff having an annular raceway formed proximally to the bead on the collar when assembled therewith, the raceway being filled with the material which is at least partially soluble in the medication or solution, the material defining the aforesaid groove which groove receives the bead of the collar.

11. In the syringe of claim 10 wherein the material is selected from the group consisting of collagens and gelatin.

12. In the syringe of claim 1 wherein the barrel carries a pre-filled quantity of the medication or solution and further comprising means for preventing contact between the medication or solution and the mounting means until the syringe is ready for use.

13. In the syringe of claim 12 wherein the collar is formed of a substantially rigid plastic material which is inert to the medication or solution.

14. In the syringe of claim 13 wherein the mounting cuff is formed of a material which is at least partially soluble in the medication or solution.

15. In the syringe of claim 14 wherein the material is selected from the group consisting of collagens and gelatin.

16. In the syringe of claim 13 wherein portions of the mounting cuff defining the groove are formed of the material which is at least partially soluble in the medication or solution.

17. In the syringe of claim 16 wherein the material is selected from the group consisting of collagens and gelatin.

18. In a syringe capable of injecting a medication or solution and having a needle, a barrel and a plunger, the improvement comprising:
   means structurally separate from and non-integral with the needle, barrel or plunger for mounting the needle to the barrel, at least portions of the mounting means being formed of a material which is at least partially soluble in the medication or solution, contact between said portions of the mounting means and the medication or solution causing the mounting means to eventually become inoperable so that the syringe can be used only a single time.

19. In the syringe of claim 18 wherein the mounting means comprise:
   a collar mounting the needle and having an annular bead formed on one end of the collar; and,
   a mounting cuff at least portions of which are formed of the material which is at least partially soluble in the medication or solution, the cuff operatively connecting the barrel of the syringe with the collar which mounts the needle, the cuff having a groove formed therein for receiving the bead of the collar and positively holding the bead therein, contact between at least portions of the cuff surrounding and defining the groove with the medication or solution causing softening of said portions to prevent maintenance of the collar and thus the needle mounted by the collar in an operative position relative to the barrel of the syringe.

20. In the syringe of claim 19 wherein the collar is formed of a substantially rigid plastic material which is inert to the medication or solution.

21. In the syringe of claim 19 wherein the mounting cuff is formed of a substantially rigid plastic material which is inert to the medication or solution, the cuff having an annular raceway formed proximally to the bead on the collar when assembled therewith, the raceway being filled with the material which is at least partially soluble in the medication or solution, the material defining the aforesaid groove which groove receives the bead of the collar.

22. In the syringe of claim 20 wherein the mounting cuff is formed of the material which is at least partially soluble in the medication or solution.

23. In the syringe of claim 20 wherein portions of the mounting cuff defining the groove are formed of the material which is at least partially soluble in the medication or solution.

24. In the syringe of claim 19 wherein that portion of the mounting cuff defining the groove comprises an interior shoulder portion of the cuff and has a second annular groove formed between the shoulder portion and inner walls of the cuff, the medication or solution contacting surfaces of the second annular groove to soften said portions.

25. In the syringe of claim 24 wherein the collar is formed of a substantially rigid plastic material which is inert to the medication or solution.

26. In the syringe of claim 18 wherein the barrel carries a pre-filled quantity of the medication or solution and further comprising means for preventing contact between the medication or solution and the mounting means until the syringe is ready for use.

* * * * *